United States Patent
Krishna et al.

(10) Patent No.: US 10,580,133 B2
(45) Date of Patent: Mar. 3, 2020

(54) TECHNIQUES FOR IDENTIFYING BLEPHAROPTOSIS FROM AN IMAGE

(71) Applicants: Viswesh Krishna, Bangalore (IN); Vrishab Krishna, Bangalore (IN)

(72) Inventors: Viswesh Krishna, Bangalore (IN); Vrishab Krishna, Bangalore (IN)

(*) Notice: Subject to any disclaimer, the term of this patent is extended or adjusted under 35 U.S.C. 154(b) by 46 days.

(21) Appl. No.: 16/139,104

(22) Filed: Sep. 24, 2018

(65) Prior Publication Data
US 2019/0370959 A1 Dec. 5, 2019

(30) Foreign Application Priority Data
May 30, 2018 (IN) .............................. 201841020273

(51) Int. Cl.
| | |
|---|---|
| *A61B 5/00* | (2006.01) |
| *A61F 9/00* | (2006.01) |
| *G06T 7/00* | (2017.01) |
| *G06T 7/73* | (2017.01) |
| *G06T 7/60* | (2017.01) |

(52) U.S. Cl.
CPC .......... *G06T 7/0012* (2013.01); *A61B 5/4887* (2013.01); *G06T 7/60* (2013.01); *G06T 7/73* (2017.01); *G06T 2207/20072* (2013.01); *G06T 2207/20081* (2013.01); *G06T 2207/30041* (2013.01); *G06T 2207/30201* (2013.01)

(58) Field of Classification Search
CPC ................ G06T 7/00; A61B 5/00; A61F 9/00
USPC .......................................................... 382/128
See application file for complete search history.

(56) References Cited

U.S. PATENT DOCUMENTS

2009/0324127 A1\* 12/2009 Budagavi ............. G06K 9/0061
382/275

OTHER PUBLICATIONS

Vahid Kazemi and Josephine Sullivan , One Millisecond Face Alignment with an Ensemble of Regression trees, published in published in 2014 IEEE Conference on Computer Vision and Pattern Recognition (CVPR), date of conference: Jun. 23-28, 2014, Electronic ISBN: 978-1-4799-5118-5.

(Continued)

*Primary Examiner* — Abolfazl Tabatabai
(74) *Attorney, Agent, or Firm* — IPHorizons PLLC; Narendra Reddy Thappeta

(57) ABSTRACT

Techniques for estimating blepharoptosis from an image of a face are disclosed. The image is captured by a camera. Histogram of Oriented Gradients and Linear Classifiers are used to predict the location of the face and eyes. An Ensemble of Regression Trees is used to detect points on each eyelid and the canthi. The location of the iris is ascertained by thresholding HLS values of individual pixels and applying a sliding window algorithm. Using regression, the eyelid shape curve is approximated. The eyelid shape curve function is used to measure the MRD1 value and distance below the limbus after detecting the Purkinje image/corneal light reflex. Finally, the intensity of blepharoptosis is estimated by categorizing the measured MRD1 and distance-from-Limbus values.

20 Claims, 8 Drawing Sheets

(56) References Cited

OTHER PUBLICATIONS

Facial point annotations, https://ibug.doc.ic.ac.uk/resources/facial-point-annotations/, retrieved from internet on Aug. 24, 2018, pp. 1-2.
Zacharym. Bodnar,Michael Neimkin, John B. Holds, Automated Ptosis Measurements From Facial Photographs, date Feb. 2016, pp. 164-150, vol. 134, No. 2.
Face landmark detection, http://dlib.net/face_landmark_detection.py.html, retrieved from Internet on Aug. 24, 2018, pp. 1-2.

* cited by examiner

TECHNIQUES FOR IDENTIFYING BLEPHAROPTOSIS FROM AN IMAGE

PRIORITY CLAIM

The instant patent application is related to and claims priority from the co-pending provisional India patent application entitled, "Techniques For Identifying Blepharoptosis From An Image", Serial No.: 201841020273, Filed: 30 May 2018, which is incorporated in its entirety herewith to the extent not inconsistent with the description herein.

BACKGROUND

Technical Field

Embodiments of the present disclosure relate generally to image processing, and more specifically to techniques for identifying Blepharoptosis from an image.

Related Art

An image generally refers to a reproduction of the form of a scene, person(s), object(s), etc., and the term 'image' includes digital images that can be rendered on electronic display devices such as a display screen of a mobile phone. Digital images that include pictures of a person can be analyzed for identification of various medical conditions with respect to the person.

Blepharoptosis refers to the abnormal drooping (or dropping down) of an eyelid over the cornea. Normally, the upper lid covers 1.0-2.0 mm of the superior part of the cornea. Blepharoptosis can be congenital or acquired. Congenital blepharoptosis results usually from isolated localized myogenic dysgenesis of the upper levator muscle. In addition to cosmetic deficits, blepharoptosis can also lead to stimulus-deprivation amblyopia. Photographic detection of blepharoptosis can be used for the prediction of amblyopia in an individual along with providing information about the levator muscle of the individual.

Several aspects of the present disclosure are directed to techniques for identifying Blepharoptosis from an image

BRIEF DESCRIPTION OF THE VIEWS OF DRAWINGS

Example embodiments of the present disclosure will be described with reference to the accompanying drawings briefly described below.

In the drawings, like reference numbers generally indicate identical, functionally similar, and/or structurally similar elements. The drawing in which an element first appears is indicated by the leftmost digit(s) in the corresponding reference number.

DETAILED DESCRIPTION

1. Summary

Figure 1:
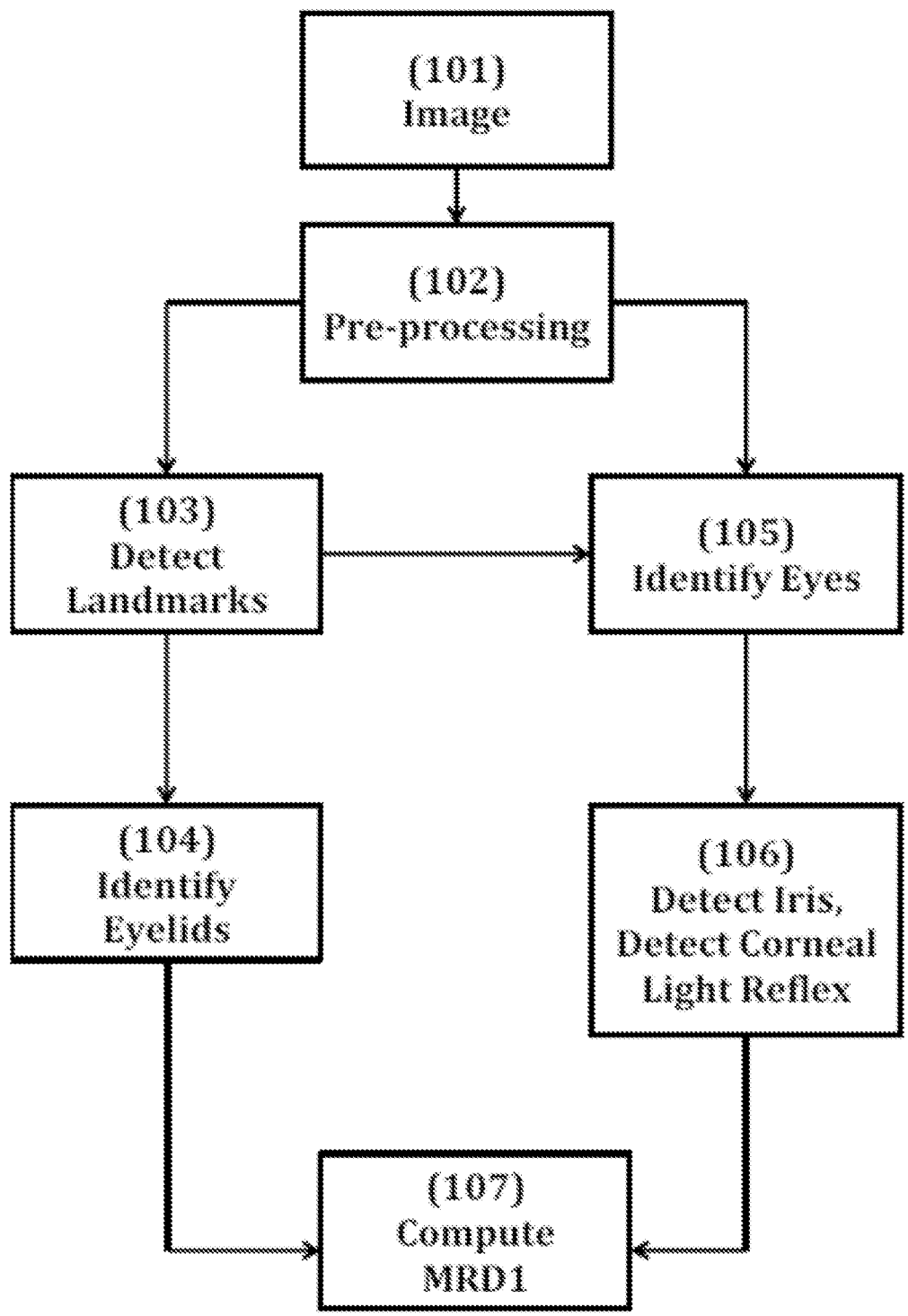
FIG. 1 is a diagram illustrating the various processing steps used for identification of blepharoptosis from an image, in an embodiment of the present disclosure.

A method for measuring blepharoptosis using an image of the face is disclosed. The method is performed under control of a hardware computer processor. The image of the face is to be captured by an image capture device with good resolution. Locations of facial landmarks (points on eyelids and canthi) are predicted using an Ensemble of Regression Trees. Regression is used to detect eyelid shape curve (e.g., quadratic, ellipsoidal or polynomial). The location of the face and eye are predicted using HOG, a linear classifier, an image pyramid and a sliding window detection scheme. Gaussian blurring is applied to remove noise. Sliding window algorithms are employed to find the iris and the corneal light reflex.

The method consists of the use of HOG (Histogram of Oriented Gradients) and linear classifiers to detect the face in the given image along with HOG and linear Classifiers to predict the location of facial landmarks in the face. With the help of these landmarks, the eyes are extracted from the image. A Linear Classifier separates entries using a linear combination of their characteristics.

Sliding window of fixed dimension (equal to the height of the eye) is passed over the length of the eye bounding box and is used to locate the iris with the help of HLS thresholding. This window is used to extract the iris and calculate its radius. The position of the corneal light reflex is also determined by a similar method, using a smaller sliding window in a small central region of each eye and finding the regions using HLS thresholding.

Using the four facial landmarks on the upper eyelid, namely two on its curvature and the other two on the nasal and ventral canthi, we can approximate the eyelid's curve using the best-fit parabola through these points. However, since the curve is aligned perpendicular to the line connecting the canthi, when an angular inclination of the canthi is present, a rotation of the axes has to be considered.

The MRD1 (Margin to Reflex 1) value can be found by calculating the difference between the y coordinates of the corneal reflex and the point on the above parabola corresponding to the x coordinate of the corneal reflex. Further, the distance of the eyelid below the limbus or the edge of the iris can be calculated knowing the radius of the iris and the MRD1 value.

This method can also be used for blink detection.

Several aspects of the present disclosure are described below with reference to examples for illustration. However, one skilled in the relevant art will recognize that the disclosure can be practiced without one or more of the specific details or with other methods, components, materials and so forth. In other instances, well-known structures, materials, or operations are not shown in detail to avoid obscuring the features of the disclosure. Furthermore, the features/aspects described can be practiced in various combinations, though only some of the combinations are described herein for conciseness.

2. Identifying Blepharoptosis

Figure 4:
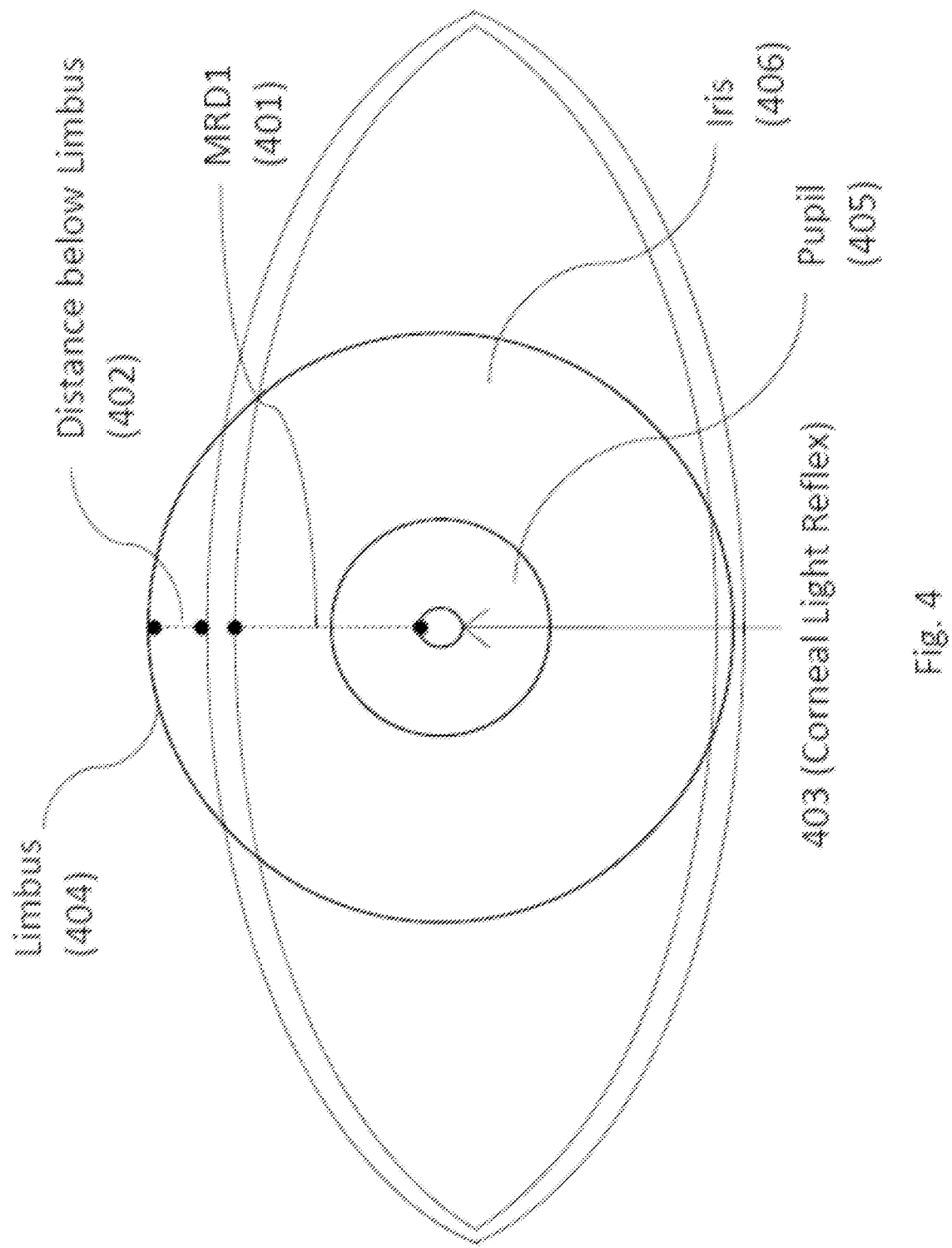
FIG. 4 is a diagram depicting the MRD1 value, corneal light reflex and the distance below the limbus in an eye, in an embodiment of the present disclosure.

Blepharoptosis may be measured using Margin to Reflex Distances (commonly referred to as MRDs) which include the MRD1, MRD2 and MRD3 values. Each of these MRD values is measured to different points of the eye from the conical light reflex. The conical light reflex (illustrated as element 403 in FIG. 4) refers to the reflection of a parallel beam of light off the cornea of the eye. The MRD1 value, which is the distance from the corneal light reflex to the midpoint of the upper eyelid, is usually measured in mm, with a value of 4-5 mm usually considered normal. MRD2 is the distance between the corneal light reflex to the midpoint of the lower eyelid. MRD3 refers to the distance from the ocular light reflex to the midpoint of the upper eyelid when the patient looks in an extreme low gaze. FIG. 4 additionally shows the limbus (404), iris (406), and pupil (405). In each of FIGS. 4, 7, and 8, the origin of the X-Y coordinate system referenced there corresponds to the left-top corner of the figure.

Another important measure for blepharoptosis is the distance to the top of the eyelid from the upper limbus of the iris. Such distance is identified as 402 in FIG. 4. The limbus as used herein refers only to the upper limbus or upper edge of the iris. The distance to the top of the eyelid from the upper limbus of the iris is usually around 1-2 mm. It is usually this value that is used to describe the intensity of drooping.

Histogram of Oriented Gradients or HOG refers to a method to find contours, edges and other changes in an image. First the gradients in the x and y directions are found using the Sobel operators. Then, the magnitude of the actual gradient along with the angle at each point is calculated. Then the image is divided into a number of cells of size 8×8, 16×16, etc., depending on the requirement and the image. The magnitudes of the gradient vectors for each of the pixels in these cells are then binned according to their angle (9 bins from 0 to 180) into a histogram. The histograms of every 4 adjacent cells form a (square) block with a common histogram. All these histograms are concatenated to form a large feature vector.

HLS is an image color space and is an abbreviation for Hue, Saturation and Lightness. It can be viewed as a cylindrical coordinate system for the RGB color space where Hue refers to the angle, Saturation the radius and Lightness the distance along the z axes. These values, in practice, usually range from 0 to 179 for Hue and 0 to 255 for Saturation and Lightness respectively. The lightness value may be the most important to find the iris. A lightness value of near zero denotes black, while one near 255 denotes white. Further, the different colors of the iris can be also incorporated by adjusting the Hue value for the required color. Converting a conventional RGB image to HLS color space is useful when a concentration of a specific color in an image is to be found.

A kernel is a certain object which is applied upon an image and returns a processed image. Kernels, like the Gaussian kernel, Laplacian kernels and others, are matrices with specific elements which correspond to their function. They can be used for edge detection, noise removal and feature detection in gray level and colored images. Kernels like those above are "convolved" or applied to each pixel in the image. While convolving an image, at a specific pixel, all the surrounding pixels are multiplied by weights defined by the values of the kernel and the pixel value is set to this sum. Kernels are also used in dilating and eroding images.

Purkinje images are reflections of objects from the structure of the eye. They are also known as Purkinje reflexes and as Purkinje-Sanson images. At least four Purkinje images are usually visible. The first Purkinje image (P1) is the reflection from the outer surface of the cornea. The second Purkinje image (P2) is the reflection from the inner surface of the cornea. The third Purkinje image (P3) is the reflection from the outer (anterior) surface of the lens. The fourth Purkinje image (P4) is the reflection from the inner (posterior) surface of the lens. Unlike the others, P4 is an inverted image. The first and fourth Purkinje images are used by some eye trackers and devices to measure the position of an eye. The corneal reflection (P1 image) used in this measurement is generally known as glint. The first Purkinje image, P1, is also known as the corneal light reflex and is used in various drooping calculations as the center of the eye.

According to an aspect of the present disclosure, Blepharoptosis is identified by measuring the distance between different parts of the eye and the eyelid. These distances are used to estimate the MRD value for both eyes (MRD1 is indicated as 401 in FIG. 4). This is done by estimating the location of the upper eyelid shape curve and the Purkinje image/corneal light reflex in the eye (402 in FIG. 4). In addition, the distance below the limbus of the eye can also be calculated knowing the radius of the iris.

FIG. 1 is a flow diagram illustrating the various processing operations or steps used for identification of blepharoptosis from an image, in an embodiment of the present disclosure.

Specifications of Image:

An image 101 of the subject is taken with an image capture device (camera). The image 101 may be generated in RGB (red, green, blue) format, well known in the relevant arts. In an embodiment, the camera has a resolution of at least 72 dpi (dots per inch). Image 101 must be dominated by the entire face and the full head. This is required so that the features of the face are preserved to ensure the machine learning models used herein are able to detect a single face in the image. In the embodiment, the image is taken with a light generating device (e.g., a "flash"), which may be required to accentuate the Purkinje image/corneal light reflex. The subject may be required to look directly at the image capture device such that the subject's gaze does not have a deviation of more than ±5° from the image capture device. The above conditions are assumed in the following steps of processing.

Pre-Processing and Noise Removal:

Pre-processing and Noise Removal are performed in step 102 of FIG. 1. Image 101 is pre-processed to remove noise and improve contrasts. Noise refers to any random variation of the brightness or color information of the image that is produced by the image capture device. Noise is removed from image 101 by smoothing the image through blurring.

A Gaussian Blur (using a Gaussian function such as the one illustrated in FIG. 6) is first applied to the image with a kernel size of 3 so as to preserve contours and edges in the image. Thereafter, a gamma correction may also be applied with a suitable value so as to make the contrast in the image sharper. Image 101, thus processed, is provided as an input to steps 103 and 105.

Figures 5, 6:
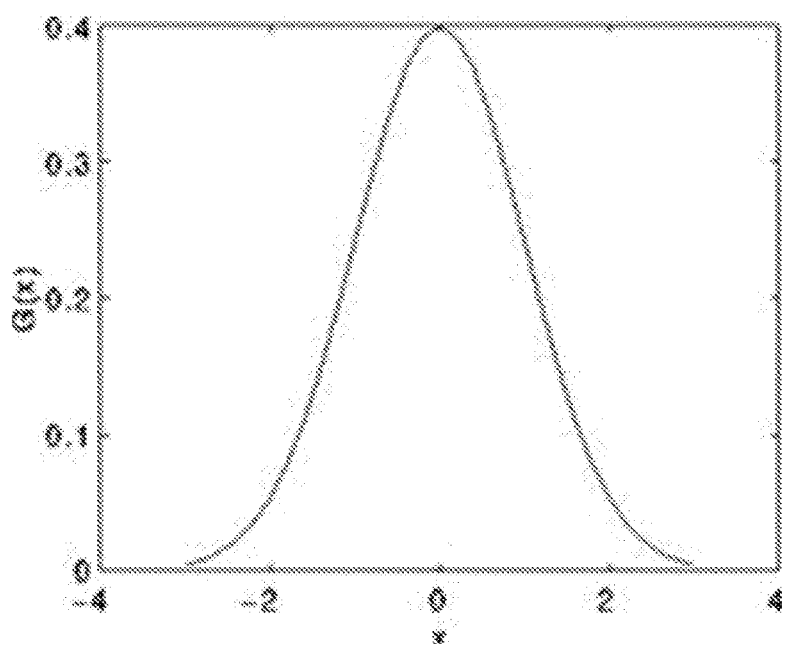
FIG. 5 is a diagram depicting the location and indexing of facial landmarks on the face of a subject, in an embodiment of the present disclosure.
FIG. 6 is a diagram illustrating a sample Gaussian distribution that is used for noise blurring of an image, in an embodiment of the present disclosure.

Facial Landmarks Detection:

In step 103, facial landmarks are detected in the image received from step 102. Facial landmark detection refers to detection of points on the eyelid and canthi by applying machine learning models. The detection of step 103 is based on the techniques employed in the Dlib object detection library to train its facial landmark detector, the details of which can be found at http://dlib.net/face_landmark_detection.py.html. Facial landmark detection consists of finding the frontal human faces in an image and estimating their pose with 68 landmarks on the face. The 68 landmarks are shown in FIG. 5. The face detector of step 103 implements the Histogram of Ordered Gradients (HOG) feature, combining this with a linear classifier, an image pyramid and sliding window detection method. The pose estimator implements an ensemble of regression trees as described in the paper 'One Millisecond Face Alignment with an Ensemble of Regression trees' by Vahid Kazemi and Josephine Sullivan, published in published in 2014 IEEE Conference on Computer Vision and Pattern Recognition (CVPR), date of conference: 23-28 Jun. 2014, Electronic ISBN: 978-1-4799-5118-5. The pose estimator was trained on the face landmark dataset authored by C. Sagonas, E. Antonakos, G, Tzimiropoulos, S. Zafeiriou, M. Pantic, in "300 faces In-the-wild challenge: Database and results, published in Image and Vision Computing (IMAVIS), Special Issue on Facial Landmark Localisation "In-The-Wild", 2016. The dataset is publicly available at https://ibug.doc.ic.ac.uk/resources/facial-point-annotations/.

The HOG feature vector of the pre-processed image is calculated and the locations of the landmarks (as indexed in FIG. 5) are obtained. The indices 37-42 on the left eye and 43-48 on the right eye shown in FIG. 5 are extracted to describe the position of the eyelids of both eyes. The details (including location) of the eyelids thus obtained are provided as inputs to step 104 as well as step 105, each described below.

Figure 2:
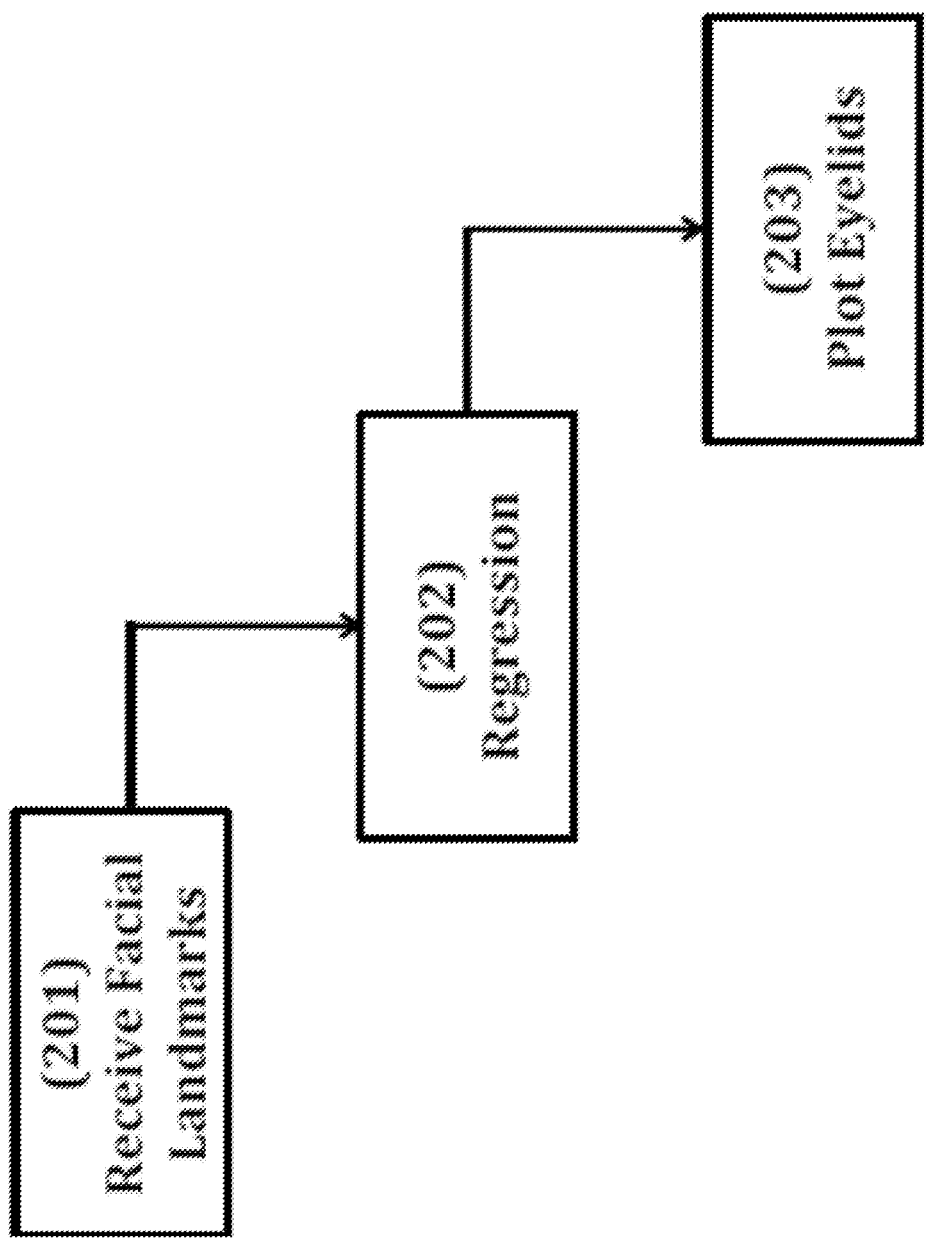
FIG. 2 is a diagram illustrating the steps employed for determining the outline of an eyelid using regression techniques in an embodiment of the present disclosure.

Regression for Eyelid Shape Curve:

In step 104, the shape curve (outline) of the eyelids identified in step 103 is determined. The eyelid shape curve refers to the contour of the junction of the eyelid with the eye, and in particular the contour of the upper eyelid herein. The position of the eyelid is required to estimate the level of blepharoptosis. Therefore, estimating/determining the eyelid plays an integral part. Eyelid shape curves can be fitted to a variety of approximation functions such as quadratic, cubic, ellipsoidal and sinusoidal. The technique for quadratic regression is described next with respect to the steps of FIG. 2.

Quadratic Regression:

The shape of the upper eyelid can be approximated to a parabola. In step 201, the facial landmark points (shown in FIG. 5, and obtained as described above) along the eyelid and the canthi are received (from step 103). The eight points indexed from 37-40 for the right eye and 43-46 for the left eye (shown in FIG. 6) are used as candidate points for quadratic regression.

In step 202, the coefficients A, B and C of the equation of the parabola $A \cdot x^2 + B \cdot x + C$ (wherein ^ represents a 'raised to power of' operation) are calculated. The matrix form of quadratic regression is used in an embodiment of the present disclosure, and is provided below:

$$\begin{pmatrix} n & \sum_{i=1}^{n} t_i & \sum_{i=1}^{n} t_i^2 \\ \sum_{i=1}^{n} t_i & \sum_{i=1}^{n} t_i^2 & \sum_{i=1}^{n} t_i^3 \\ \sum_{i=1}^{n} t_i^2 & \sum_{i=1}^{n} t_i^3 & \sum_{i=1}^{n} t_i^4 \end{pmatrix} \begin{pmatrix} c_1 \\ c_2 \\ c_3 \end{pmatrix} = \begin{pmatrix} \sum_{i=1}^{n} d_i \\ \sum_{i=1}^{n} d_i t_i \\ \sum_{i=1}^{n} d_i t_i^2 \end{pmatrix} \quad \text{Equation 1}$$

wherein, n represents the number of eye landmarks (here n=4), $t_i$ represent the x-coordinate or abscissa of the eye landmarks, $d_i$ represent the y-coordinates or ordinates of the eye landmarks, and $c_i$ represent the coefficients of the quadratic equation.

Figure 7:
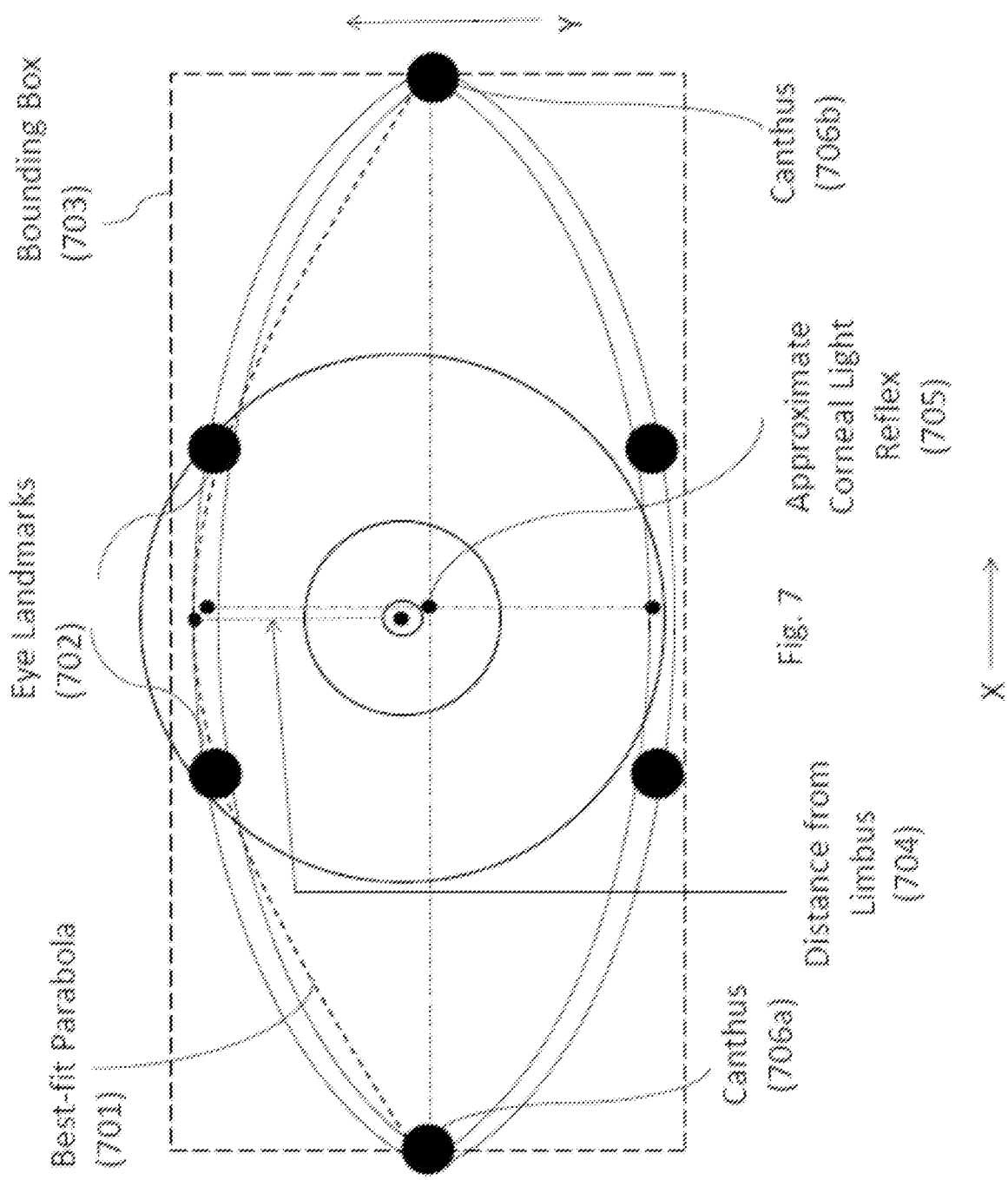
FIG. 7 is a diagram depicting the eye landmarks (702), bounding box (703), best-fit parabola (701), the approximate corneal light reflex (705), canthi (706*a* and 706*b*) and the approximate distance from limbus (704) for an eye, in an embodiment of the present disclosure.
Figure 8:
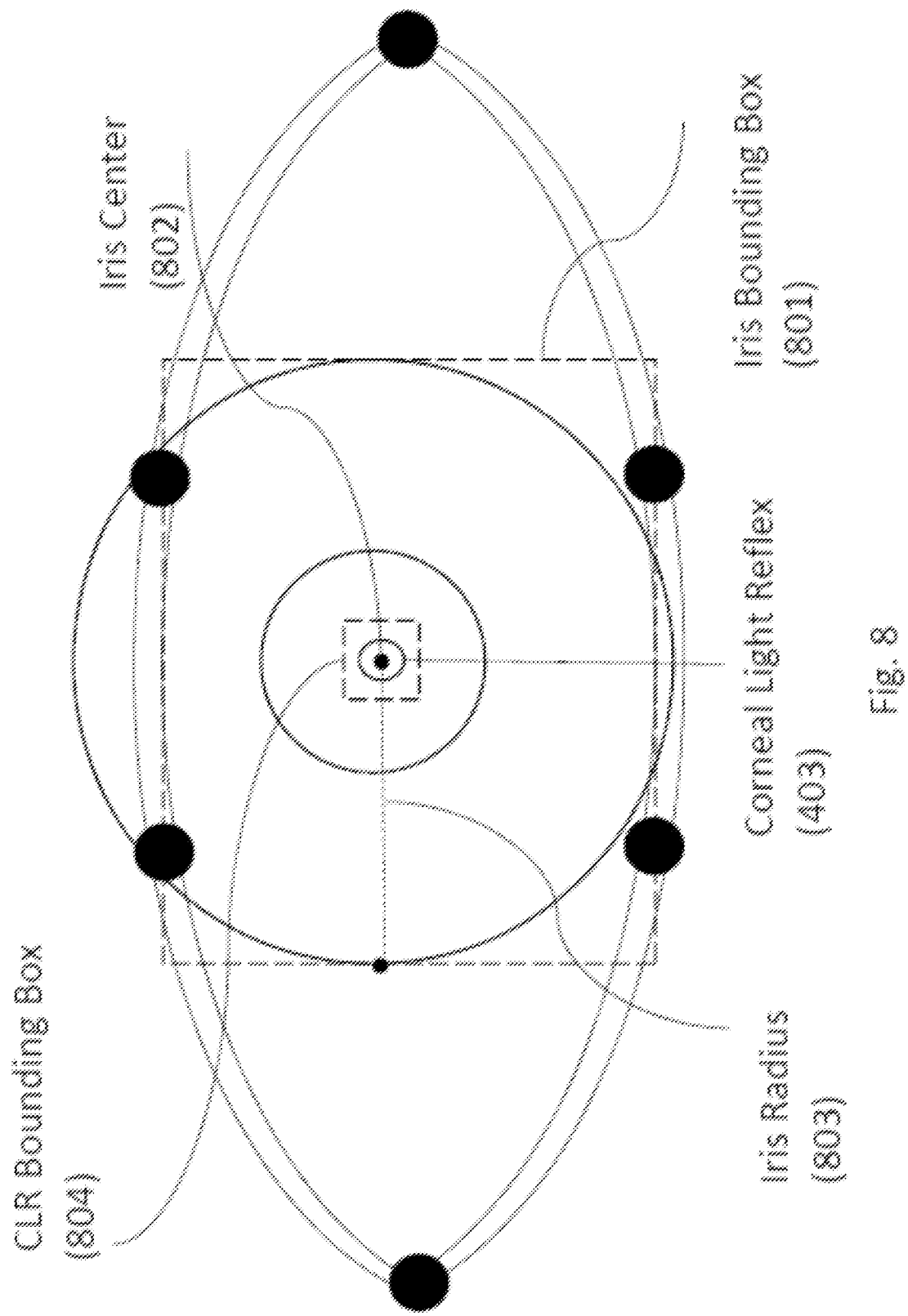
FIG. 8 is a diagram depicting the iris bounding box, the corneal light reflex bounding box, the iris center and iris radius for an eye, in an embodiment of the present disclosure.

The quadratic equation, with coefficients A, B and C determined according to Equation 1, approximates the eyelid shape curve especially well at the peak of the eyelid, the region where MRD1 is calculated. The best fit parabola, thus obtained, is plotted on image 101 (as illustrated in FIG. 7), and the quadratic equation is passed to the MRD calculation model of step 107, described below.

In an alternative embodiment of the present disclosure, ellipsoidal regression is used to obtain the eyelid shape curve, as described next.

Ellipsoidal Regression:

As in quadratic regression, an ellipse can be fit through the candidate points on the upper eyelid. The lengths of the semi-major and semi-minor axes of the best-fit ellipse in the equation $x^2/a^2 + y^2/b^2 = 1$ are to be calculated. These lengths are estimated using the matrix form of ellipsoidal regression, not shown herein, but which is well-known in the relevant arts. The obtained best-fit ellipse is plotted on image 101, and the elliptical equation passed to the MRD calculation model.

In step 203, the parabola or ellipse is plotted/graphed on image 101, and the coefficients of the equation are passed to the subsequent models, as noted above.

Eye Extraction:

In step 105, the position of the eyes of the subject are identified from the processed image received from step 102, and the positions of the facial landmarks received from step 103. Using the location of the facial landmarks (shown in FIG. 5) indexed from 37-42 for the right eye and 43-48 for the left eye, the eyes of the subject are identified. The horizontal limits of the eye are defined to be the position of the canthi. The vertical limits cannot be defined as the maximum vertical distance between the candidate points on the upper and lower eyelids because the entire eyelid and iris would not be considered as a region of interest. This is because the region of the eyelid between 38-39 and 44-45 (shown in FIG. 5) would be cut off by considering only the facial landmarks. Instead, the vertical dimensions of the bounding box around the eye are increased by a constant factor proportional to the maximum vertical distance between the candidate points on both eyelids. A constant factor is used to estimate the portion of the eyelid outside the bounding box as the size of the eyelid is in proportion to the size of the eye, which is approximated by the dimensions of the bounding box. In another embodiment of the present disclosure, the maximum value of the quadratic equation obtained from step 104 is computed to ascertain the top of the eyelid, and thus find the vertical dimensions of the bounding box of the eye. The position of the eyes thus obtained is provided as an input to step 106.

Figure 3:
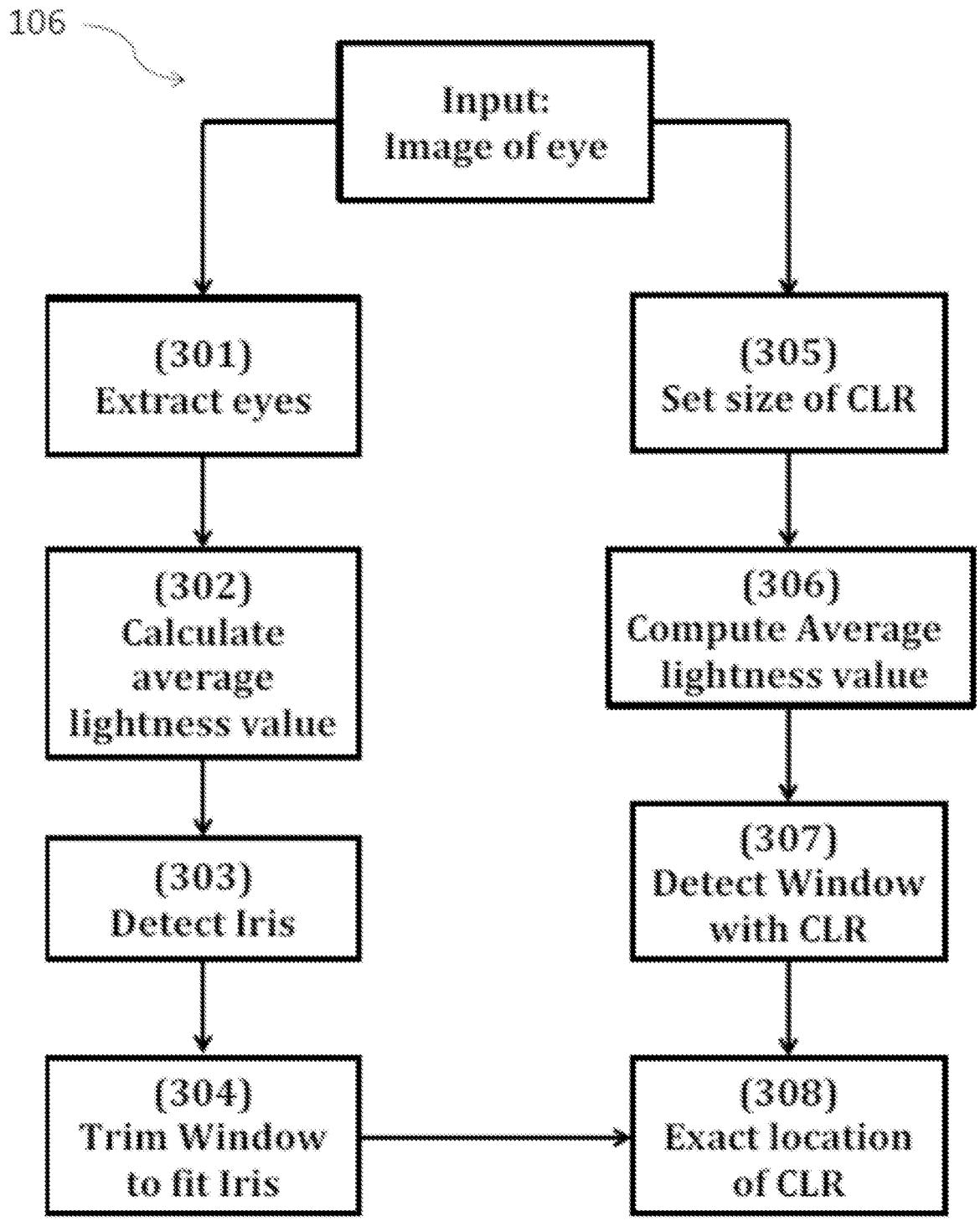
FIG. 3 is a diagram illustrating the steps for determining the location of the iris and subsequently the corneal light reflex from an image, in an embodiment of the present disclosure.

Iris and Corneal Light Reflex Detection:

Step 106 is used to compute Iris and Corneal Light Reflex, and contains two sub-processes. The first sub-process (containing steps 301-304 of FIG. 3) determines the bounding box for the irises (of both eyes) of the subject, while the second sub-process (containing steps 305-308 of FIG. 3) determines the bounding box of the Purkinje image or the corneal light reflex. FIG. 3 shows the various steps of the sub-processes of step 106.

Iris Bounding Box Detection:

The iris of the eye (and consequently the dimensions of the square bounding box) can be approximated to the height of the eye for convenience. In step 301, the eyes are extracted from image 101 using the positions and dimensions returned from step 105. In step 302, a HLS format of image 101 is obtained from the RGB format. The average Lightness value (HLS) (described above) of all the pixels in the eye bounding box is calculated and multiplied by a factor to threshold the image. Thus, a HLS-thresholded image is obtained. The hue of the image can be used to detect irises of various colors. The angle representing hue can be classified (i.e., compared against various thresholds) to identify the different iris shades in humans. The output of step 302 is a modified and thresholded grayscale image.

In step 303, a sliding-window algorithm (not described herein, but well known in the relevant arts) detects the iris as the region with the highest concentration of dark-colored pixels (wherein darkness is defined with the Lightness value from HLS).

In step 304, the window (obtained from the operation of step 303) is trimmed to fit the iris. Trimming refers to a fine adjustment of the boundaries of the eye bounding box. For each edge of the HLS-thresholded image (obtained in step 302), a sum of pixel values within a predetermined range and straddling that edge is obtained. The edges are then respectively moved to that position at which the sum crosses a pre-determined threshold for that edge. Thus, each edge is shrunk towards the center of the bounding box (indicated as element 801 of FIG. 8) till it encounters the iris of the eye (detected using the dark-colored pixels.) The center of the iris is defined to be the geometrical center of the bounding box, or in other words, the point of intersection of the diagonals of the bounding box (as indicated by element 802 of FIG. 8). The radius of the iris is defined to be half the horizontal size (i.e. the width) of bounding box 801 of the iris (and is indicated by element 803 of FIG. 8). The vertical size of the bounding box cannot be used to calculate the radius of the iris as the iris is generally occluded by the upper and lower eyelids. The radii and centers of the irises are provided as inputs to step 107 (FIG. 1) to be used for calculating the MRD1 value.

Corneal Light Reflex/Purkinje Image Bounding Box Detection:

Detection of the bounding box for the Corneal Light Reflex (CLR) is similar to the detection of iris bounding box detection.

In step 305, the size of the CLR is approximated to one-fifth the radius of the iris (calculated in step 304).

In step 306, the average Lightness value (HLS) of all the pixels is calculated as in step 302. Here, the scaled average lightness value is approximated by a linear model that effectively describes the higher lightness value required for detecting the CLR.

In step 307, a sliding window algorithm is used to detect the window containing the CLR by detecting the region with the highest concentration of light-colored pixels.

In step 308, the exact location of the CLR is detected by once again thresholding the image with the average lightness value in the window. A weighted average (with the weight defined as the lightness value which can take on the values 0 or 1) of the coordinates in the window provides a closer estimate for the location of the CLR to be used as a reference point for the center of the eye. A bounding box (CLR bounding box) is then drawn on image 101 (and as indicated by element 804 of FIG. 8). The location of the CLR is passed to 107 for calculating the MRD1 value.

In step 308, when flash is not used to capture image 101, the location of the CLR (approximate CLR 705 in FIG. 7) can also be approximated using the location of the canthi (706a and 706b in FIG. 7) and the eyelid shape curve (701). The X coordinate of the approximated CLR (705) is defined to be the arithmetic mean of the X coordinates of the two canthi for the given eye. The Y coordinate of the CLR is then defined to be the sum of the radius of the iris (803 in FIG. 8) and the height of the lower eyelid shape curve at the X coordinate of the approximated CLR (705). Thus, the Y coordinate is an iris radius above that of the lower eyelid at the X coordinate of the approximated CLR. A bounding box (804 in FIG. 8) for the CLR is then drawn and the location of the CLR is passed to 107 for calculating the MRD1 value.

MRD1 Calculation:

Step 107 receives the regression equation approximating the upper eyelid from step 104 and the location of the center and radius of the iris and the position of the CLR from step 106. As noted above, MRD1 value is the distance between the point on the upper eyelid above the CLR and the CLR, and is indicated by element 401 of FIG. 4. The x-coordinate (horizontal location) of the CLR is passed as an argument to the regression equation to calculate the y-coordinate (vertical location) of the eyelid above the CLR. The vertical distance between the two points measures the pixel length between the two points. This pixel length is then converted to a distance measured in millimeters. This is accomplished by using the iris radius as a standard. The iris diameter is known to be approximately constant for humans across ages at approximately 11.46 mm. As the pixel length of the iris radius is known, a scaling factor to convert all pixel lengths in the image to distances can be calculated. On multiplying the pixel length between the two points by the above calculated scaling factor, the MRD1 value for the eye is obtained.

Then, the radius of the iris and the above measured MRD1 value are used to estimate the occlusion of the limbus (edge of the iris, indicated in FIG. 4) by the eyelid. The distances of the eyelid from the limbus (indicated by element 402 in FIG. 4) and the MRD1 value (401) have medically accepted ranges, and are used herein to classify a subject with mild, moderate and severe blepharoptosis, as noted below. The ranges are listed below and are taken from the Electronic Journal of Ophthalmology (www.ejournalofopthalmology-.com/ejo/ejo13.html).

Severity of Blepharoptosis Based on Distance (402) of Top of Eyelid from Limbus:

Distance 402 being less than or equal to 2 mm indicates mild blepharoptosis.

Distance 402 equal to 3 mm indicates moderate blepharoptosis.

Distance 402 being equal to or greater than 4 mm indicates severe blepharoptosis.

Severity of Blepharoptosis Based on MRD1 (401) Values:
MRD1 (401) being greater than or equal to 4 mm indicates mild blepharoptosis.
MRD1 (401) of 3 mm indicates moderate blepharoptosis.
MRD1 (401) being equal to or less than 2 mm indicates severe blepharoptosis.

3. Digital Processing System

Figure 9:
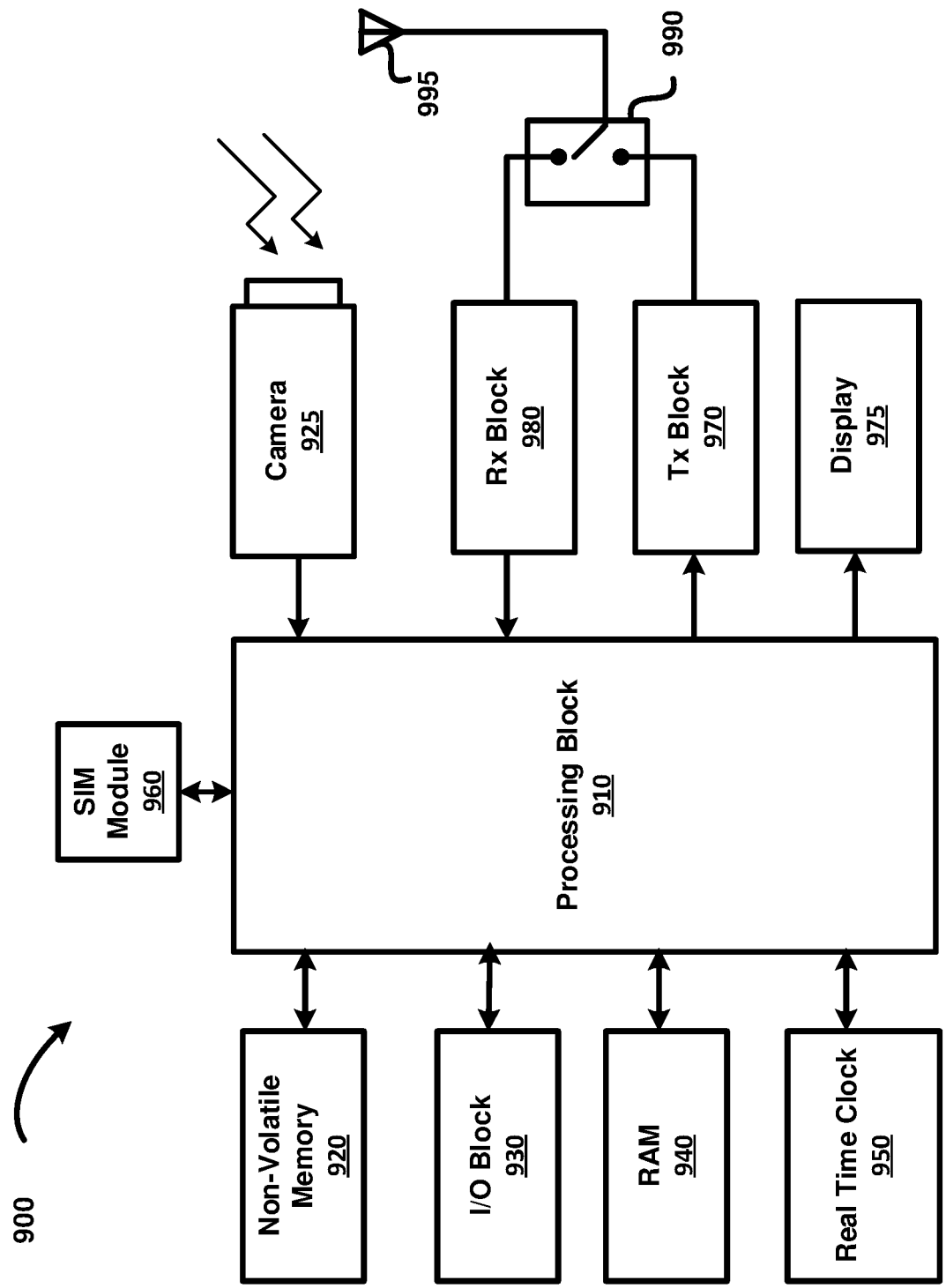
FIG. 9 is a block diagram of a device in which several aspects of the present disclosure can be implemented.

FIG. 9 is a block diagram representing a digital processing system (which can be, for example, a mobile phone) in which several aspects of the present disclosure can be implemented. Mobile phone 900 is shown containing processing block 910, non-volatile memory 920, camera 925, input/output (I/O) block 930, random access memory (RAM) 940, real-time clock (RTC) 950, SIM (Subscriber Identity Module) module 960, transmit (Tx) block 970, receive (Rx) block 980, display 975, switch 990, and antenna 995. Some or all units of mobile phone 900 may be powered by a battery (not shown). The specific blocks of mobile phone 900 are shown by way of illustration only, and mobile phone 900 may contain more or fewer blocks depending on specific requirements. One or more of the blocks of FIG. 9 may be implemented in integrated circuit (IC) form. Although the digital processing system of FIG. 9 is noted as a mobile phone, it is to be understood that, in general, the digital processing system can be any digital device (e.g., laptop, personal digital assistant, etc.) having a camera.

SIM module 990 is designed to identify the specific subscribers and related parameters to facilitate the subscriber to access various services provided via a wireless communication network. In an embodiment, SIM module 960 contains a physical holder (into which a SIM card (SIM), can be inserted) and processing block 910 retrieves various data parameters stored on the inserted SIM cards. A SIM card may provide the international mobile subscriber identity (IMSI) number (also the phone number) used by a network operator to identify and authenticate a subscriber. Typically, the SIM is 'inserted' into such holder before mobile phone 900 can access the services provided by the network operator for the subscriber configured on the SIM. Additionally, a SIM may store address book/telephone numbers of subscribers, security keys, temporary information related to the local network, a list of the services provided by the network operator, etc.

Processing block 910 may read the IMSI number, security keys etc., in transmitting and receiving voice/data via Tx block 970 and Rx block 980 respectively. The SIM in SIM module 990 may subscribe to data and voice services according to one of several radio access technologies such as GSM, LTE (FDD as well as TDD), CDMA, WCDMA, 5G, etc., as also noted above.

RTC 950 operates as a clock, and provides the 'current' time to processing block 910. Additionally, RTC 950 may internally contain one or more timers. I/O block 930 provides interfaces for user interaction with mobile phone 900, and includes input devices and output devices. The input devices may include a keypad and a pointing device (e.g., touch-pad). The output device may correspond to, for example, a communications port, such as a serial port.

Antenna 995 operates to receive from, and transmit to, a wireless medium, corresponding wireless signals (representing voice, data, etc.) according to one or more standards such as LTE. Switch 990 may be controlled by processing block 910 (connection not shown) to connect antenna 995 to one of blocks 970 and 980 as desired, depending on whether transmission or reception of wireless signals is required. Switch 990, antenna 995 and the corresponding connections of FIG. 9 are shown merely by way of illustration. Instead of a single antenna 995, separate antennas, one for transmission and another for reception of wireless signals, can also be used.

Tx block 970 receives, from processing block 910, digital signals representing information (voice, data, etc.) to be transmitted on a wireless medium (e.g., according to the corresponding standards/specifications), generates a modulated radio frequency (RF) signal (according to the standard), and transmits the RF signal via switch 990 and antenna 995. Tx block 970 may contain RF circuitry (mixers/up-converters, local oscillators, filters, power amplifier, etc.) as well as baseband circuitry for modulating a carrier with the baseband information signal. Alternatively, Tx block 970 may contain only the RF circuitry, with processing block 910 performing the modulation and other baseband operations (in conjunction with the RF circuitry).

Rx block 980 represents a receiver that receives a wireless (RF) signal bearing voice/data and/or control information via switch 990, and antenna 995, demodulates the RF signal, and provides the extracted voice/data or control information to processing block 910. Rx block 980 may contain RF circuitry (front-end filter, low-noise amplifier, mixer/down-converter, filters) as well as baseband processing circuitry for demodulating the down-converted signal. Alternatively, Rx block 980 (the receive chain) may contain only the RF circuitry, with processing block 910 performing the baseband operations in conjunction with the RF circuitry.

Camera 925 represents an image-capture device, and can be operated by a user to take pictures. Specifically, image 101 (FIG. 1) of a subject is captured using camera 925. Camera 925 forwards data representing the captured image (which would include face of the subject) to processing block 910 for processing, as described in detail above, to detect blepharoptosis.

Display 975 is used for displaying images, such as for example, the face of a subject as noted above. Additionally, display 975 may be used for displaying various other objects such as icons, applications, etc. Display 975 may be implemented to have a touch-sensitive screen to allow a user to select displayed objects, navigate to other views, etc. In particular, display 975 may be used to display image 101, as well as the details of FIGS. 4, 5, 7 and 8.

Non-volatile memory 920 is a non-transitory machine readable medium, and stores instructions, which when executed by processing block 910, cause mobile phone 900 to operate as described herein. In particular, the instructions enable mobile phone 900 to operate as described with respect to the flowchart of FIG. 1. The instructions may either be executed directly from non-volatile memory 920 or be copied to RAM 940 for execution.

RAM 940 is a volatile random access memory, and may be used for storing instructions and data. RAM 940 and non-volatile memory 920 (which may be implemented in the form of read-only memory/ROM/Flash) constitute computer program products or machine (or computer) readable medium, which are means for providing instructions to processing block 910. Processing block 910 may retrieve the instructions, and execute the instructions to provide several features of the present disclosure.

Processing block 910 (or processor in general) may contain multiple processing units internally, with each processing unit potentially being designed for a specific task. Alternatively, processing block 910 may represent a single processing unit executing multiple execution threads. Processing block (or circuitry) 910 performs (in addition to other tasks) the operations of the steps of FIGS. 1, 2, and 3. In general, processing block 910 executes instructions stored in non-volatile memory 950 or RAM 940 to enable mobile phone 900 to operate according to several aspects of the present disclosure, described in detail herein.

4. Conclusion

References throughout this specification to "one embodiment", "an embodiment", or similar language means that a particular feature, structure, or characteristic described in connection with the embodiment is included in at least one embodiment of the present disclosure. Thus, appearances of the phrases "in one embodiment", "in an embodiment" and similar language throughout this specification may, but do not necessarily, all refer to the same embodiment.

While various embodiments of the present disclosure have been described above, it should be understood that they have been presented by way of example only, and not limitation. Thus, the breadth and scope of the present disclosure should not be limited by any of the above-described embodiments.

What is claimed is:

1. A method of measuring the intensity of blepharoptosis of eyelids of a subject from an image of the face of the subject, the method being implemented in a digital device, the method comprising:
   detecting the location of the face and eyes of said subject in said image;
   generating an eye bounding box for an eye of said subject using facial landmarks determined during said detecting;
   determining the location of the iris in said eye bounding box as being the region with lowest pixel intensity in a first color range for said eye;
   identifying the Corneal Light Reflex (CLR) in said iris as that group of pixels in said iris that have the highest intensity value in said iris;
   setting a shape of the upper eyelid of said eye by applying regression with respect to corresponding ones of said facial landmarks on said upper eyelid;
   computing a distance between said CLR and the point on said upper eyelid at which a vertical line passing through said CLR intersects said upper eyelid,
   wherein said distance is indicative of said intensity of blepharoptosis.

2. The method of claim 1, wherein said detecting employs a Histogram of Ordered Gradients (HOG) and Machine Learning Classifiers to detect said location of said face and said eyes utilizing a plurality of facial landmarks.

3. The method of claim 1, wherein said determining employs a sliding-window technique.

4. The method of claim 3, wherein said determining further comprises:
   translating said image from RGB (Red, Green, Blue) format to HLS (Hue, Saturation, Lightness) color space; and
   using said image in said HLS color space to identify said region with lowest pixel intensity in a first color range, said identifying yielding an HLS-thresholded image.

5. The method of claim 4, wherein said determining further comprises:
   corresponding to an edge of the HLS-thresholded image, computing a sum of pixel values within a predetermined range and straddling said edge; and
   shifting said edge to that position at which said sum crosses a pre-determined threshold.

6. The method of claim 1, wherein said setting employs one of quadratic and ellipsoidal regression.

7. The method of claim 1, wherein when flash is not used to capture said image, said CLR is approximated as the point whose X coordinate is the mean of the two canthi of said eye, and whose Y coordinate is an iris radius above that of the lower eyelid at said X coordinate.

8. A device comprising:
   a camera to generate an image of the face of a subject;
   a processor block and a memory,
   said memory to store instructions which when retrieved and executed by said processor block causes said device to perform the actions of:
      detecting the location of the face and eyes of said subject in said image;
      generating an eye bounding box for an eye of said subject using facial landmarks determined during said detecting;
      determining the location of the iris in said eye bounding box as being the region with lowest pixel intensity in a first color range for said eye;
      identifying the Corneal Light Reflex (CLR) in said iris as that group of pixels in said iris that have the highest intensity value in said iris;
      setting a shape of the upper eyelid of said eye by applying regression with respect to corresponding one of said facial landmarks on said upper eyelid;
      computing a distance between said CLR and the point on said upper eyelid at which a vertical line passing through said CLR intersects said upper eyelid,
      wherein said distance is indicative of said intensity of blepharoptosis.

9. The device of claim 8, wherein said detecting employs a Histogram of Ordered Gradients (HOG) and Machine Learning Classifiers to detect said location of said face and said eyes utilizing a plurality of facial landmarks.

10. The device of claim 8, wherein said determining employs a sliding-window technique.

11. The device of claim 10, wherein said determining further comprises:
    translating said image from RGB (Red, Green, Blue) format to HLS (Hue, Saturation, Lightness) color space; and
    using said image in said HLS color space to identify said region with lowest pixel intensity in a first color range, said identifying yielding an HLS-thresholded image.

12. The device of claim 11, wherein said determining further comprises:
    corresponding to an edge of the HLS-thresholded image, computing a sum of pixel values within a predetermined range and straddling said edge; and
    shifting said edge to that position at which said sum crosses a pre-determined threshold.

13. The device of claim 8, wherein said setting employs one of quadratic and ellipsoidal regression.

14. The device of claim 8, wherein when flash is not used to capture said image, said CLR is approximated as the point whose X coordinate is the mean of the two canthi of said eye, and whose Y coordinate is an iris radius above that of the lower eyelid at said X coordinate.

15. A non-transitory machine readable medium storing one or more sequences of instructions in a digital processing system for measuring the intensity of blepharoptosis of eyelids of a subject from an image of the eyes of said subject, wherein execution of the one or more instructions by one or more processors contained in said digital processing system enables said digital processing system to perform the actions of:
- detecting the location of the face and eyes of said subject in said image;
- generating an eye bounding box for an eye of said subject using facial landmarks determined during said detecting;
- determining the location of the iris in said eye bounding box as being the region with lowest pixel intensity in a first color range for said eye;
- identifying the Corneal Light Reflex (CLR) in said iris as that group of pixels in said iris that have the highest intensity value in said iris;
- setting a shape of the upper eyelid of said eye by applying regression with respect to corresponding one of said facial landmarks on said upper eyelid;
- computing a distance between said CLR and the point on said upper eyelid at which a vertical line passing through said CLR intersects said upper eyelid,
- wherein said distance is indicative of said intensity of blepharoptosis.

16. The non-transitory machine readable medium of claim 15, wherein said detecting employs a Histogram of Ordered Gradients (HOG) and Machine Learning Classifiers to detect said location of said face and said eyes utilizing a plurality of facial landmarks.

17. The non-transitory machine readable medium of claim 15, wherein said determining employs a sliding-window technique.

18. The non-transitory machine readable medium of claim 17, further comprising instructions for:
- translating said image from RGB (Red, Green, Blue) format to HLS (Hue, Saturation, Lightness) color space; and
- using said image in said HLS color space to identify said region with lowest pixel intensity in a first color range, said identifying yielding an HLS-thresholded image.

19. The non-transitory machine readable medium of claim 18, further comprising instructions for:
- corresponding to an edge of the HLS-thresholded image, computing a sum of pixel values within a predetermined range and straddling said edge; and
- shifting said edge to that position at which said sum crosses a pre-determined threshold.

20. The non-transitory machine readable medium of claim 15, wherein when flash is not used to capture said image, said CLR is approximated as the point whose X coordinate is the mean of the two canthi of said eye, and whose Y coordinate is an iris radius above that of the lower eyelid at said X coordinate.

* * * * *